United States Patent [19]
Hovde et al.

[11] Patent Number: 5,804,702
[45] Date of Patent: Sep. 8, 1998

[54] PROCESS FOR REDUCING INTERFERING SIGNALS IN OPTICAL MEASUREMENTS OF WATER VAPOR

[75] Inventors: David Christian Hovde; Daniel J. Kane; Joel A. Silver, all of Santa Fe, N. Mex.

[73] Assignee: Southwest Sciences Incorporated, Santa Fe, N. Mex.

[21] Appl. No.: 799,228

[22] Filed: Feb. 14, 1997

Related U.S. Application Data

[60] Provisional application No. 60/011,657 Feb. 14, 1996.
[51] Int. Cl.[6] ....................................................... G01N 7/00
[52] U.S. Cl. ............................................ 73/24.04; 250/343
[58] Field of Search ............................ 73/24.04, 25.04, 73/29.01; 250/343

[56] References Cited

U.S. PATENT DOCUMENTS

| | | | |
|---|---|---|---|
| 4,133,836 | 1/1979 | Nissen et al. | 568/569 |
| 4,228,034 | 10/1980 | Butler et al. | 252/430 |
| 4,405,905 | 9/1983 | Busca et al. | 331/94.1 |
| 4,515,612 | 5/1985 | Burrus et al. | 65/3.12 |
| 4,544,378 | 10/1985 | Coe et al. | 55/68 |
| 4,583,997 | 4/1986 | Staudigl | 55/31 |
| 4,620,909 | 11/1986 | Keyser et al. | 204/157.22 |
| 4,875,945 | 10/1989 | Penzhorn et al. | 376/146 |
| 4,935,196 | 6/1990 | Griesbach et al. | 376/314 |
| 5,319,955 | 6/1994 | Chastagner | 73/19.02 |
| 5,381,429 | 1/1995 | Minemoto et al. | 372/21 |

Primary Examiner—Hezron E. Williams
Assistant Examiner—Jay L. Politzer
Attorney, Agent, or Firm—Jeffrey D. Myers

[57] ABSTRACT

A process for improving moisture analyzers or hygrometers that use optical absorption techniques to measure water vapor. Water vapor in the optical path outside the sample region is treated to exchange the hydrogen atoms for deuterium, so that the adsorbed water vapor is converted to heavy water, $D_2O$, and isotopically mixed HDO, thus reducing or eliminating the interference in any optical absorption apparatus for measuring water vapor, provided the spectral resolution is sufficient to resolve normal water absorptions from heavy water absorptions.

52 Claims, 4 Drawing Sheets

PROCESS FOR REDUCING INTERFERING SIGNALS IN OPTICAL MEASUREMENTS OF WATER VAPOR

GOVERNMENT RIGHTS

The U.S. Government has a paid-up license in this invention and the right in limited circumstances to require the patent owner to license others on reasonable terms as provided for by the terms of Small Business Innovative Research (SBIR) Contract No. 50-DKNB-5-00189 awarded by the U.S. Department of Commerce.

CROSS-REFERENCE TO RELATED APPLICATIONS

This application claims the benefit of the filing of Provisional Application Ser. No. 60/011,657, entitled "Process for Reducing Interfering Signals in Optical Measurements of Water Vapor", filed on Feb. 14, 1996 now abandoned.

BACKGROUND OF THE INVENTION

1. Field of the Invention (Technical Field)

The present invention relates to the analysis of gases for detection and quantification of water vapor, in particular, to reducing the interfering effects of the water vapor that is present as a contaminant in the optical path of an absorption spectrometer.

2. Background Art

Measurement of water vapor is important in many fields, including industrial processing and studies of the atmosphere. Many methods have been devised to measure water vapor.

Optical absorption-based methods have the advantage of a high degree of specificity to water vapor, fast time response, and a wide range of concentrations that can be accurately measured. Optical absorption methods quantify the amount of water vapor in an optical path by measuring the decrease in light intensity across that path. The light can be broadband or monochromatic, and it can be in the microwave, infrared, visible or ultraviolet spectral region. The optical path of an absorption spectrometer can be represented schematically as consisting of a frequency selected source such as a laser, a glow bar in combination with a diffraction grating, or a lamp in combination with Fourier transform spectrometer, a sample region, and a detector. The total water vapor absorbance signal that is produced by an absorption spectrometer is proportional to the sum of the absorbances generated in the total optical path, which includes the source, sample region, and detector. The source path can be less than 1 mm in the case of a laser diode or light emitting diode or 1 m path in high resolution Fourier transform or grating spectrometers.

A problem with these optical measurements is the presence of water vapor in the source or detector, which contributes an optical absorbance signal or interfering signal that adds to that from the sample being measured. Water vapor rapidly contaminates any surface exposed to the atmosphere and is extremely difficult to remove. The magnitude of the interfering signal depends on the specific temperature, pressure, and concentration of gases in each region and on the detection technique employed. The problem of interfering signals is particularly severe when the sample absorbance is small, because then the source and detector must also generate very low absorbance. This case arises in atmospheric measurements at high altitude and in the analysis of trace moisture contamination of semiconductor process gases. This unwanted water vapor signal is a source of error in the analytic measurement.

Optical absorption methods for measuring water vapor include instruments using a glow bar and an interference filter (Bayly et al., U.S. Pat. No. 4,033,699 (1977)), glow bar and monochromator (Nelson, Ophir Corp., Navy SBIR Contract no. N00019-85-C-0033), light emitting diode and filter (Wilson et al., Rev. Sci. Instrum. 66, 5618 (1995)), Fourier transform infrared spectrometer (Stallard et al., J. Electrochem. Soc. 142, 2777 (1995); Pivonka, Appl. Spectrosc. 45, 597 (1991); Toth, Appl. Opt. 22, 908 (1983); Toth, J. Opt. Soc. Am. B, 10, 2006 (1993); Gamache et al., J. Mol. Spectrosc. 170, 131 (1995); and Midac Corp. product literature), and a diode laser (Arroyo et al., Appl. Opt. 33, 3296 (1994); Mucha and Barbalas, ISA Transactions 25, 25 (1986)).

Various techniques have been devised to suppress the unwanted water vapor interference signals. Existing methods for removing this interfering signal require large quantities of purge gas, bulky external vacuum components, intermittent measurements, high pressures, high temperature, or chemical getters.

The approach taken by Stallard and by Pivonka is simply to purge the apparatus with extremely dry gas to keep the background water vapor signals at a low and stable value. In addition to consuming large quantities of purge gas, this method is slow: several weeks were required to reach a low, stable value in the work of Stallard.

Midac Corporation (Irvine, Calif.) presently markets a hygrometer for measuring trace moisture levels in semiconductor gases that is based on a Fourier transform infrared spectrometer. The interfering signal is reduced by maintaining a vacuum of $10^{-5}$ Torr in the optical path outside the sample region. This high vacuum design adds significantly to the cost of building the instrument and also makes it difficult to check the optical alignment.

Gamache uses a computer algorithm to subtract out the interfering signal present in an evacuated FT-IR spectrometer. However, this requires that the sample gas can be removed so that its contribution to the background can be measured, which limits the time response and may even be impractical in the case of moisture measurement at the parts per billion sensitivity level. In the approach used by Mucha, the sample gas is at a significantly lower pressure from the other parts of the apparatus, so that the differences in spectroscopic line shape can be used to suppress the interference signal. This approach requires that the sample pressure be significantly different from the pressure in other parts of the optical path, and it only can be applied when the spectrometer can resolve these line shape differences.

Chemical getters can be used, but they require an inert atmosphere and may contribute significant bulk to small components such as a diode laser or a detector. Baking and pumping the surfaces removes a substantial portion of water vapor from surfaces previously exposed to air (Wheeler, Physics Today, 52 (August 1972)), but the residual water vapor can still degrade the accuracy of the optical measurement. Moreover, the heat required can destroy some materials or cause warping or misalignment of the optical apparatus. Cooling can be used to reduce the vapor pressure of water, but significantly increases the size and complexity of the instrument.

It is clear from the prior art that water vapor contamination is a problem in optical humidity measurements, and that the existing methods devised to address this issue suffer from various drawbacks, including the following: long purge times; the need to use ultrahigh vacuum equipment; the requirement to evacuate the sample region to measure a background spectrum; limited sample pressure range; the need for high spectral resolution; the use of high temperatures; the need for bulky packaging; or the need to maintain a low temperature.

The problem of water vapor contamination of surfaces is also well known. Water vapor can be trapped in microcracks even in polished metals and only slowly released. Surface treatments to prevent the adsorption of water onto surfaces are of limited effectiveness, and may not provide the optical properties needed for the source or detector. The rate of release of water vapor from the surfaces is extremely slow, resulting in a continuous "virtual leak." However, the exchange of isotopes with the trapped water vapor is well known (Dobrozemsky, presentation at "Water: Its Measurement and Control in Vacuum," NIST, Gaithersburg, Md. (May, 1994), and Ulenikov et al., J. Mol. Spectrosc. 170, 1 (1995)). This approach has even been used to study the kinetics of water transfer from surfaces.

Additionally, a related problem in the field of fiber-optic communications is absorbance by hydroxyl groups in optical fibers, which causes a reduction in the distance that light can be transmitted through the fiber. This unwanted absorbance in the fiber can be reduced through the use of isotopic substitution of deuterium for hydrogen, as it is well known that the vibrational frequencies are changed by isotopic substitution. Two processes are known which address this problem by modifying the isotopic composition of a solid substance, the OH groups bonded to the optical fiber. Burrus and Stone (U.S. Pat. No. 4,515,612 (1985) used the diffusion of deuterium gas ($D_2$) followed by an elevated temperature of at least 300° C. to convert the OH in the fiber to OD. Staudigl (U.S. Pat. No. 4,583,997 (1986)) treated the auxiliary gases from which the optical fiber material is manufactured. This treatment consisted of flowing the auxiliary gas through $D_2O$, for instance by bubbling, to convert the residual water in the gas to heavy water. This step was followed by a drying step to reduce the total water content of the gas.

SUMMARY OF THE INVENTION
(DISCLOSURE OF THE INVENTION)

In the present invention, the isotopic composition of water vapor in the optical path is modified to reduce or eliminate contamination. The invention includes a method for reducing interference signals in an optical absorption apparatus for measuring water vapor, comprising the steps of exchanging hydrogen atoms in the water vapor in the apparatus with a source of labile deuterium, whereby adsorbed water vapor is converted to heavy water; and sealing the apparatus, whereby reintroduction of water is prevented. The invention further includes a specially designed apparatus for reducing interference signals in an optical absorption apparatus for measuring water vapor, which comprises means for converting hydrogen atoms in water vapor in the optical apparatus into heavy water. This means for converting, in one embodiment, may comprise a gas manifold means connected to a source region in the apparatus. The gas manifold means applies an isotopic substitution process to the source region in order to perform the conversion.

A primary object of the present invention is to reduce or eliminate the water vapor optical absorption signals that arise from portions of the optical path that do not contain the sample gas.

Another object of the invention is to improve the accuracy and facilitate the detection of trace moisture levels.

Another object of the invention is to allow the spectrometer to be operated without the need for purge gases.

Another object of the invention is to permit the use of standard component package designs and standard materials with little or no mechanical modification.

Another object of the invention is to permit the use of any convenient sample pressure.

Another object of the invention is to permit continuous measurement of samples.

Another object of the invention is to permit the rapid quantification of trace moisture levels.

A primary advantage of the present invention is the provision of a simple, low cost method for reducing the background signals from enclosed regions in the optical path in measurements of water vapor using optical absorption. The process can be applied at the time of manufacture or in the field. Once the process has been applied, no purge gases are required and no restrictions are placed on the pressure of the gas sample to be measured. The process can be implemented in any instrument that can resolve the spectral features of light water from those of heavy water. Little or no physical modification should be necessary to implement this approach in FT-IR spectrometers, near-infrared diode lasers, and room temperature detectors such as InGaAs detectors. Implementation of this process should permit a significant increase in the accuracy of optical measurements of trace moisture levels, which will directly benefit the fields of high altitude atmospheric chemistry and analytical chemistry for the semiconductor gas industry. In addition, this process can be used inside lamps and glowbars to reduce the effects of water vapor on their emission spectra.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

Figure 1:
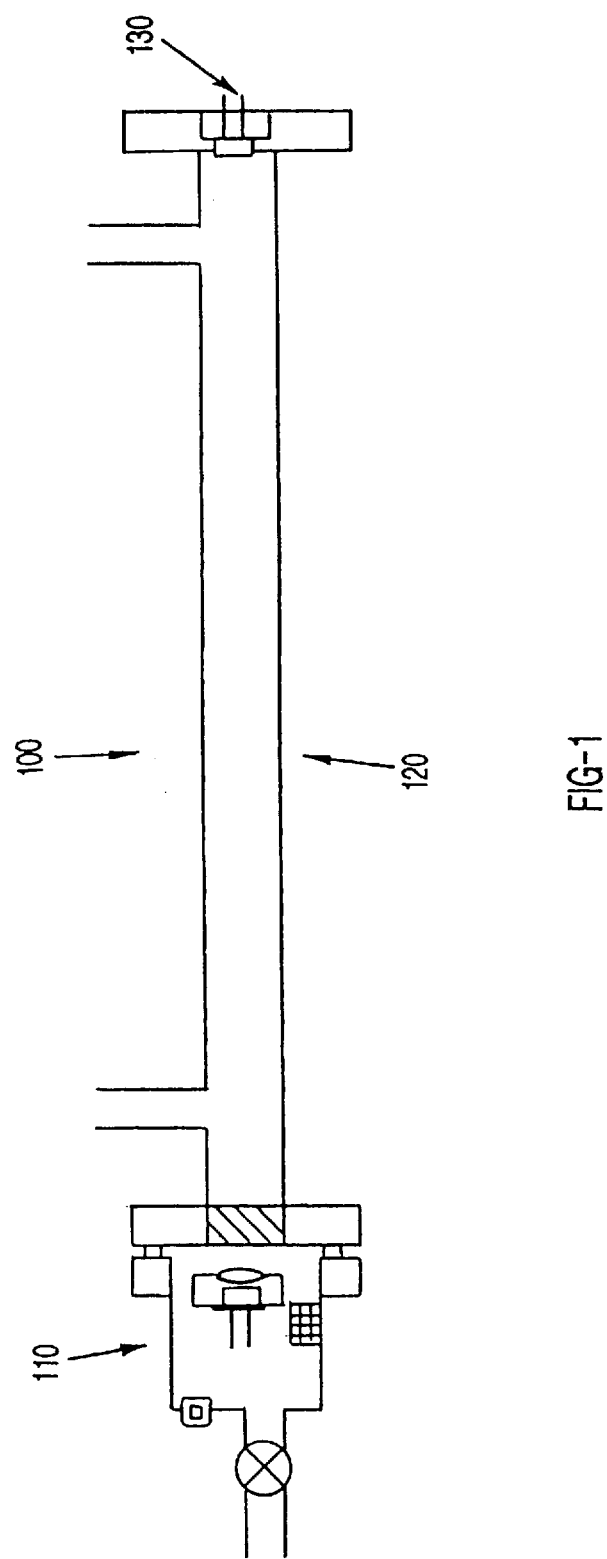
FIG. 1 is a cross-sectional view of a diode laser spectrometer.

DESCRIPTION OF THE PREFERRED
EMBODIMENTS (BEST MODES FOR
CARRYING OUT THE INVENTION)

The present invention is a method and apparatus for reducing water vapor interference signals in optical absorption apparatus for extended periods of time. This interference signal arises from water vapor that is present in some portion of the apparatus outside the sample path, for instance in the source or the detector. The sources of this unwanted water vapor are the humidity in the atmosphere and the surfaces of the components of the optical apparatus. In its preferred embodiment, the method of the invention consists of (1) exchanging the hydrogen atoms in the water vapor in the source or detector region with a source of labile deuterium, so that the adsorbed water vapor is converted to heavy water, $D_2O$, and isotopically mixed HDO, then (2) sealing the region to prevent reintroduction of $H_2O$ of normal isotopic composition from the atmosphere.

In implementing the present invention, the first step is to expose a selected portion of the spectrometer to a substance with labile deuterium atoms (atoms that can exchange rapidly at room temperature). The source of labile deuterium may be varied and can be a vapor, a liquid, or a solid. Possible substances include pure deuterium gas, $D_2$, with a suitable catalyst for enhancing isotope exchange with surface water, deuterated acid gases such as DCl (deuterated hydrogen chloride) and DBr (deuterated hydrogen bromide), deuterated basic gases such as $ND_3$ (deuterated ammonia), and deuterated liquids such as heavy water, $D_2O$. Alternative sources of labile deuterium include the use of heavy water treated with acids or bases, or the liquid or vapor of deuterated alcohols such as methanol, $CH_3OD$, or deuterium containing crystals such as $CaSO_4.2D_2O$. $D_2O$ vapor is preferred. It is convenient, low cost, and chemically identical to the water vapor already present in the system. It poses no unusual hazards in handling and will not damage the optical components. For instance, diode lasers can safely be exposed to $D_2O$ vapor.

The methods of applying the treatment include soaking parts of the source or detector in a liquid such as heavy water prior to drying and assembly, pouring the liquid inside a part of the source or detector and permitting the vapor to saturate the inner surfaces prior to drying and assembly, flowing vapor past the inside surface of the source or detector, and evacuating the air, then introducing a vapor.

The spectral absorption features of heavy water are different from those of regular water. This process can reduce the interference in any optical absorption apparatus for measuring water vapor, provided the spectral resolution is sufficient to resolve normal water absorptions from heavy water absorptions. The method of the invention can be applied to all or part of the optical path of the spectrometer; the process can be performed at the time of manufacture of the complete spectrometer or its sub-assemblies, or it can be performed when the spectrometer is in use.

Optional process steps include removing excess heavy water vapor prior to sealing, and including a deuterium-doped desiccant to act as a long term isotopic ballast.

The optional second step is to remove moisture from the selected portion, for instance by pumping out the gas with a vacuum pump or by purging with a source of dry nitrogen. Purging is accomplished by flowing dry gas past the inner surfaces of the treated part. The gas or the part may be heated to facilitate drying.

Over time, the H atom concentration may rise due to leaks or slow desorption of water trapped in deep crevices that have not been completely isotopically exchanged. To maintain a high D/H ratio and hence ensure the long term reliability of the process, an additional process step can be added. This step consists of introducing into the source or detector chamber a source of labile deuterium with a low water vapor pressure. This source acts as a "reservoir" or isotope ballast. Possible sources include a molecular sieve which has been treated by equilibration with $D_2O$ vapor or a deuterated salt such as $CaSO_4.2D_2O$. This deuterium source would be chosen to have sufficient mass such that the D/H ratio value would remain sufficiently close to unity for the anticipated lifetime of the water vapor sensor. In addition, the kinetics for isotope exchange should be faster than the rate at which the unexchanged water is released into the gas phase.

In the preferred embodiment of the apparatus of the invention a gas manifold specifically designed for the conversion of the hydrogen atoms in the water vapor into heavy water is applied to the spectrometer. The drawings supplied depict the preferred embodiment of the apparatus of the invention as well as acting as a guide to understanding the theoretical basis for the invention.

FIG. 1 is a cross-sectional view of a diode laser spectrometer 100 consisting of a source 110, a sample region 120, and a detector 130. Light passes from the source 110 (shown as a laser diode) through the sample region 120 (which may be open to the atmosphere, or enclosed as shown), and onto the detector 130 (shown as a photodiode). Both the source region and the detector are sealed to prevent exchange of water vapor with the ambient atmosphere.

Figure 2:
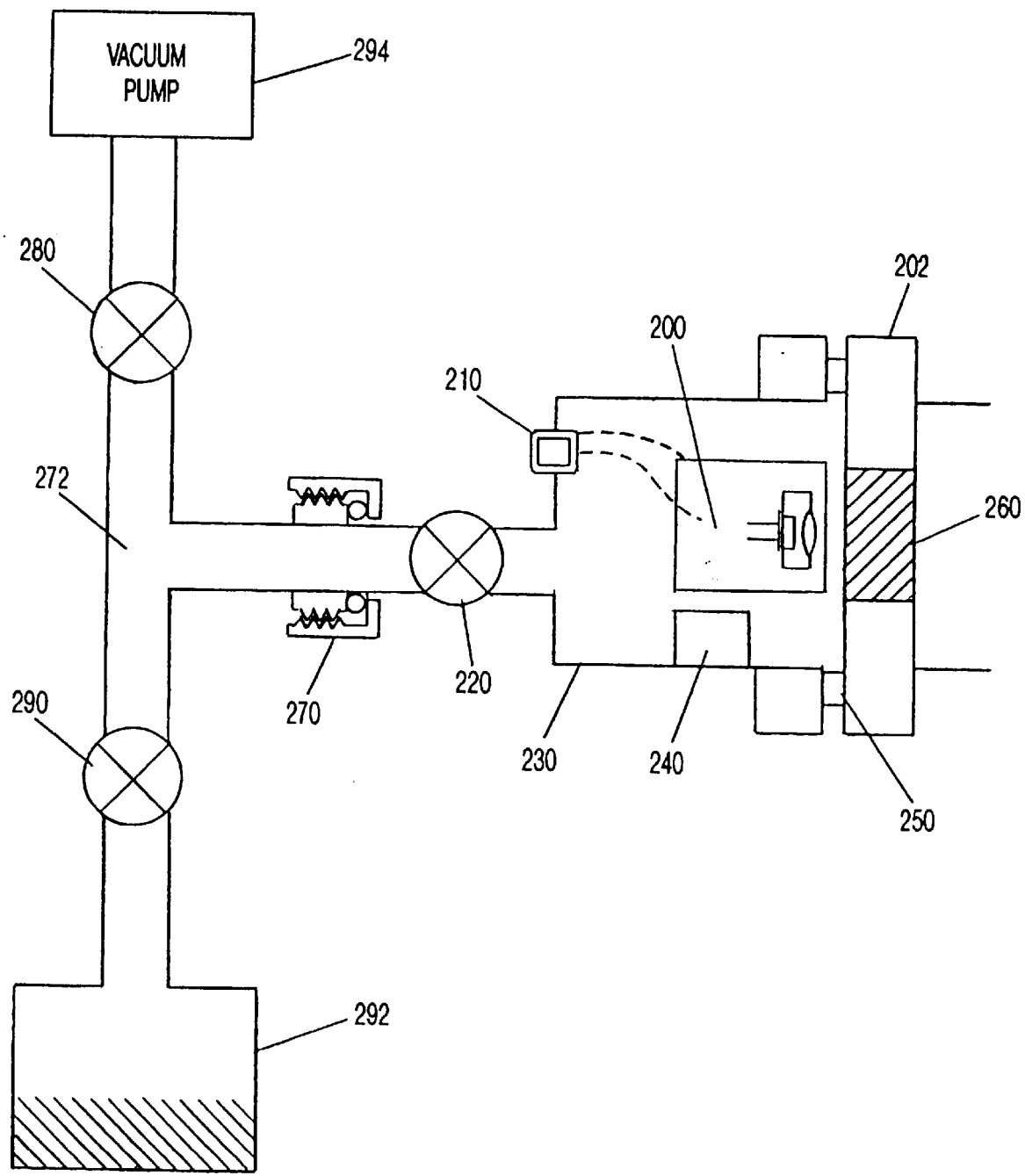
FIG. 2 is a cross-sectional view of the source region and gas manifold that can be used to implement the method of present invention.

FIG. 2 is a detailed cross-sectional view of the source region 110 shown connected to a gas manifold 272 that illustrates one approach for applying the present invention. The source region is shown as a laser diode assembly 200 that is sealed from the ambient atmosphere by way of a flange 202 such as CF-type flange available from NorCal Products, Yreka, Calif. and other vendors, an electrical feedthrough 210 such as Model MCF-075-1 from NorCal, a valve 220 such as bellows valve from Nupro Co. Willoughby, Ohio, a housing 230, a gasket 250 such as a copper gasket, and a window 260 for instance, a glass window. The source region is attached by a demountable flange 270 such as a Cajon UltraTorr fitting to the gas manifold 272. The gas manifold can be constructed from glass, stainless steel, copper or brass following standard vacuum techniques so that it can be evacuated by a vacuum pump 294 and then exposed to a source of heavy water ($D_2O$) 292. Heavy water is commercially available in 99.8% isotopic purity from Johnson Matthey, Waltham Mass. and others. The source region also contains a wire cannister 240 made from wire mesh and containing approximately 5 g $CaSO_4$ available from W. A. Hammond Drierite Co., Xenia Ohio.

The gas manifold 272 shown in FIG. 2 can be used to apply the isotopic substitution process to the source region 110. Valves 220 and 280 are opened to evacuate the source region. Valve 280 is then closed, and valve 290 is opened, admitting $D_2O$ vapor to the source region 110, then valve 290 is closed. The quantity of $D_2O$ admitted to the source should be no more than 0.26 grams per gram of $CaSO_4$. Optionally, valve 280 may then be opened to evacuate the source region again before closing valve 220 to isolate the source region 110 from the gas manifold. The source region may then be removed from the gas manifold by disconnecting vacuum connector 270.

Figure 3:
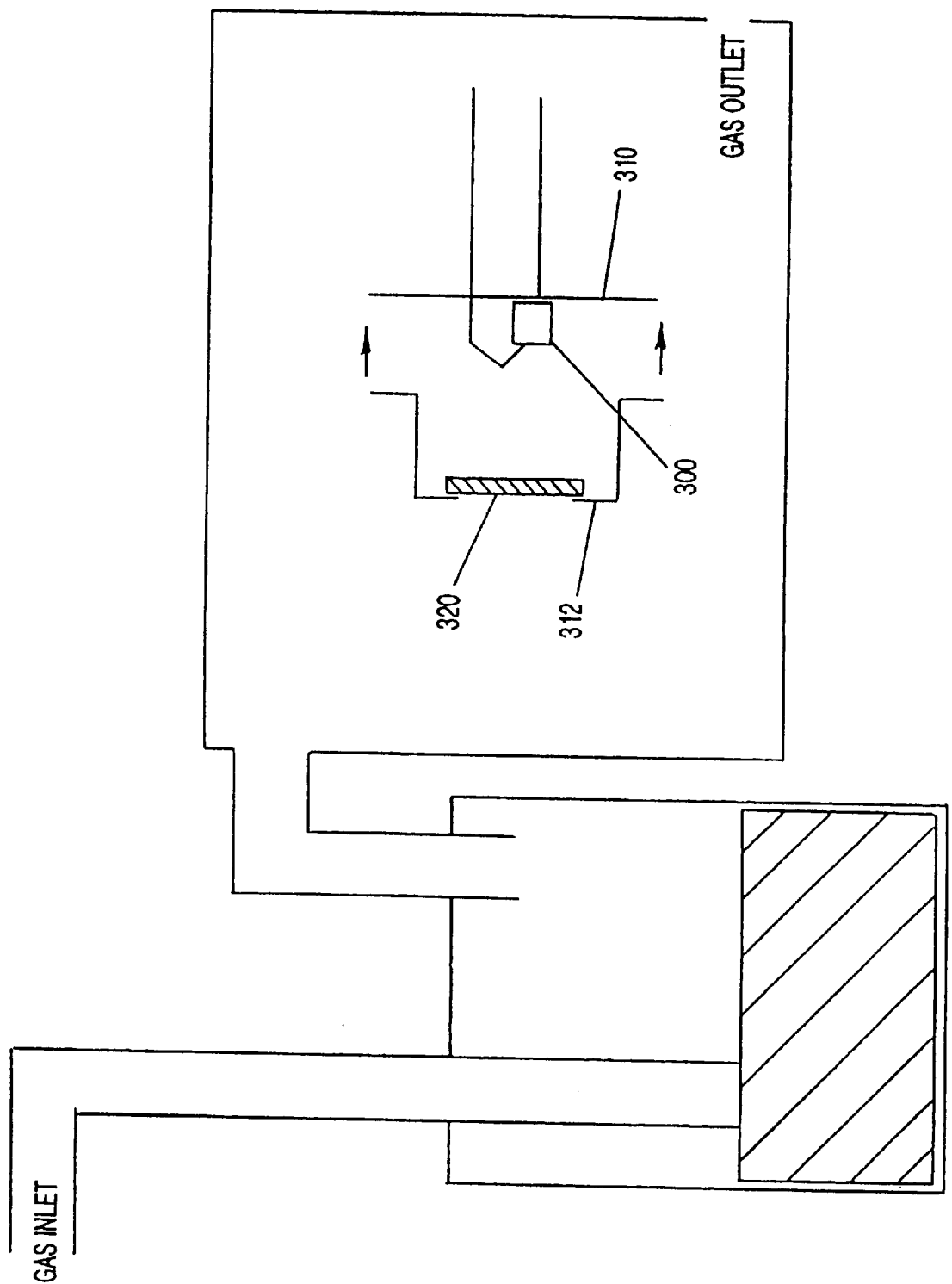
FIG. 3 is a cross-sectional detail of the photodiode showing a method for implementing the present invention.

FIG. 3 is a cross-sectional detail of the photodiode demonstrating how it can be processed using the present invention without need to modify mechanical design of the detector. The detector is shown as photodiode 300 mounted in a partially assembled TO-5 standard electrical package 310 and 312 with an optical window 320. To apply the invented process, the parts of the detector are exposed to an atmosphere containing $D_2O$ vapor at a concentration preferably in the range between 1 and 20 Torr. A suitable atmosphere can be produced by bubbling dry nitrogen through $D_2O$ and flowing this gas through an enclosure that contains the vapor and the detector assembly, such as a glove box. After allowing sufficient time to saturate the internal surfaces of the parts with $D_2O$, an optional step is to remove excess $D_2O$, for instance by flowing dry nitrogen across the parts. Finally, the detector is hermetically sealed, for instance by using an adhesive, by soldering, or by crimping.

Figure 4:
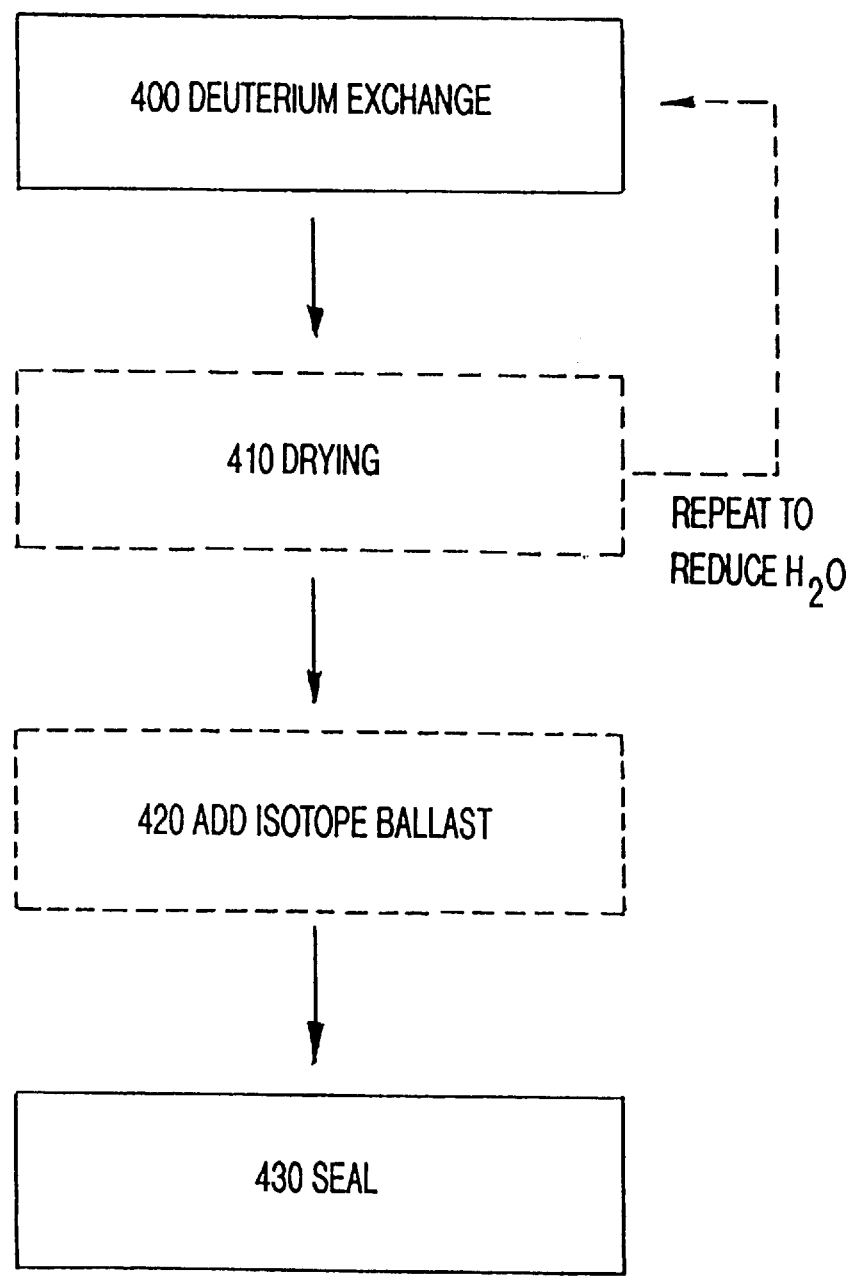
FIG. 4 is a flow chart indicating the steps involved in the preferred embodiment of the process of the invention.

FIG. 4 is a flow chart indicating the steps involved in the preferred embodiment of the process of the invention, including deuteration 400, optional drying 410, optional addition of an isotope ballast 420, and sealing 430. Optional steps are shown as dashed boxes. The steps of drying 410 and sealing 430 are well known in the production of sources and detectors. The present invention adds the step 400 of deuterium exchange and the optional step 420 of adding an isotope ballast.

The basis of isotopic substitution is that naturally occurring water vapor consists primarily of $H_2O$, with only trace amounts of deuterium-containing or heavy water. The reaction to exchange isotopes,

$$H_2O+D_2O \leftrightarrows 2HDO \qquad (1)$$

is rapid and results in an equilibrium distribution of components, based on the initial concentrations of each species and the temperature of the system. Similar exchange reactions interconvert the isotopes of water with those of other labile deuterium containing compounds, such as deuterated ammonia ($ND_3$) or deuterated hydrogen chloride (DCl). (Labile atoms are those that are easily exchanged.) At room temperature, the total amounts of the three forms of water can be represented from a statistical model. If the fraction of labile hydrogen in the form of deuterium atoms is given by x and the remainder, 1−x, is present as H, then the amounts are just $$[H_2O]=(1-x)^2 [W]$$
$$[HDO]=2x(1-x) [W] \qquad (2)$$
$$[D_2O]=x^2 [W] \qquad (2)$$

The square braces denote gas phase concentrations for each isotope and [W] is the sum of the concentrations of all three isotopes. In the presence of excess $D_2O$, virtually all of the $H_2O$ can be converted to HDO. Equation 2 predicts that for 90% exchange of deuterium (x=0.9), the residual water present as $H_2O$ will be 1% of the concentration without the isotopic treatment. Heavy water is available commercially as a liquid with isotopic purity of greater than 99.8% (x=0.998) so [$H_2O$] can be suppressed tremendously.

Because this invention applies to absorption spectrometers used to measure water vapor, some background on the spectroscopy is needed to calculate the performance advantage to be expected from the process. The contribution of each portion of the spectrometer to the measured absorbance signal can be determined by first calculating the absorption cross section as a function of wavelength using published spectroscopic parameters such as those in the HITRAN database (Rothman et al., J. Quant. Spectrosc. Radiat. Transf. 48, 469 (1992)) together with measurements of the composition, pressure, temperature, and optical path length in each portion. From the absorbances, the spectrometer signal response can be calculated, although the details of this calculation depend on the particular spectrometer used. For the case of a wavelength-modulated single frequency diode laser spectrometer, the absorbances from each section are added together to produce the total absorbance, and then the modulation response is computed (Silver, Appl. Opt. 31, 707 (1992)). If the calculated interfering signal arising from the source or detector region is greater than or comparable to the sample absorbance signal, then the sensitivity of the measurement will be improved by the invented interference reduction process. If the interfering signal is comparable to the desired instrument accuracy, then the accuracy of the measurement will be improved by interference reduction.

The actual improvement in the sensitivity or accuracy will depend on the extent to which the exchange of isotopes can be made complete (see above) and how much the spectrometer distinguishes heavy water vapor (containing at least one deuterium atom) from normal water vapor. The spectrometer will still show an unwanted interference signal that depends on the heavy water concentration and the spectrometer response to $D_2O$ and HDO. The absorption cross sections are calculated again to determine the spectrometer response. For the case of a single frequency diode laser spectrometer, the spectrometer response to heavy water is negligible. This results in the highest suppression of interfering signals. The suppression achieved for other spectrometer designs can be evaluated using the procedure outlined above.

Because the isotope equilibration reaction is so fast, the duration required for the first treatment step will depend on transport processes. These are governed by the geometry and materials of the spectrometer part being treated and by the method of delivering the deuterium. The time does not need to be significantly longer than that required for diffusion throughout the treated part. However, the time can be made considerably shorter, for instance by entraining the $D_2O$ vapor in a carrier gas such as dry nitrogen that is made to flow past the part at atmospheric pressure, by flowing the pure $D_2O$ past the part at reduced pressure, by evacuating the air from the part, then introducing pure $D_2O$ vapor, to increase the diffusion constant, by causing turbulent mixing through local heating of a portion of the part, or by other mechanical or physical methods known to promote rapid mixing.

The preferred embodiment illustrates how the isotope exchange process can be applied to reduce the interfering signal generated in a component of a spectrometer. Due to the great variety of spectrometer designs to which this process could be applied, the method of implementing this process will vary.

Alternatively, the treatment could be performed in a vacuum compatible apparatus as in the source treatment example above, or parts could be assembled in a glove box or other controlled atmosphere as in the detector treatment example above.

The entire source or detector assembly could be treated after construction, or all or part of it could be processed at some earlier stage of fabrication. For instance, aluminum parts could be stored in liquid $D_2O$ prior to assembly. The source of deuterium could be a vapor, a liquid, or a solid.

Alternatively, the deuterium treatment may be improved by heating, thermally cycling, or mechanically vibrating the region to be processed, as these processes all influence water vapor transport. Ultraviolet, visible infrared, or microwave light may be directed to the inner surfaces of the region to be processed, as these treatments can enhance water vapor exchange to improve the speed and completeness of the isotope treatment. For instance, the Phototron ultraviolet source from Danielson Associates, Lisle Ill. may be used during the isotope exchange process.

Industrial Applicability

The invention is further illustrated by the following non-limiting examples.

EXAMPLE 1

Results obtained in the use of spectrometers without the invented process demonstrated and quantified the effects of water vapor contamination on optical measurements. In one instance, the water vapor inside a commercial diode laser operating at a wavelength near 1400 nm and packaged according to military specification MIL-883C for package moisture gave rise to an optical absorbance of about $10^{-3}$, or about 500 times larger than other sources of optical noise in a well designed instrument. The optical path inside the laser source was approximately 1 mm. The instrument performance with this commercially packaged laser was unacceptable, and a costly redesign of the laser housing was required.

EXAMPLE 2

In another instance of using a standard spectrometer arrangement, a background water vapor signal was traced to water vapor present in the reference detector of a dual beam spectrometer. This water vapor signal could be reduced by cooling the reference detector housing, as expected due to the very strong temperature dependence of the vapor pressure of water. The optical path length through the detector portion of the spectrometer was approximately one millimeter. It would be difficult and expensive to redesign the housings for the laser and detector to reduce their optical path lengths to 0.01 mm, which is the path length required to reduce the water vapor signal to negligible or undetectable levels.

EXAMPLE 3

A test of the method of the invention was conducted using a diode laser operating near 1400 nm, using a strong $H_2O$ feature to measure the presence of water by wavelength modulation spectroscopy as described by Silver. The diode laser was mounted inside an electro-polished stainless steel vacuum chamber with a volume of 4 liters that contained copper and anodized aluminum parts and PVC insulated wiring. After pumping out the chamber with a liquid nitrogen trapped mechanical pump, the $H_2O$ water vapor signal inside the chamber was measured. The vacuum chamber was then filled with 12 Torr $D_2O$ vapor and permitted to stand for 10 minutes, then it was again pumped out. After one treatment, the $H_2O$ signal dropped to 25% of its original value. After five such treatments, the $H_2O$ signal dropped to 1.7% of its original value. Such a suppression was sufficient to reduce the background to acceptable levels in a diode-laser based device for measuring trace water vapor down to levels of 1 part per billion in semiconductor process gases.

EXAMPLE 4

In a second test of the technique of the invention, a 38 cm long cell consisting of electro polished stainless steel with glass windows was treated by pouring approximately 5 ml of liquid $D_2O$ (isotopic purity 99.8%) into it. The cell was closed and allowed to stand for one week, after which the excess liquid was poured out. The cell was then dried by purging with dry nitrogen for 20 minutes, and the cell was evacuated to a total pressure of 1 Torr. No $H_2O$ interference signal was detectable from this cell using a wavelength modulated diode laser spectrometer operating near 1400 nm wavelength. For comparison, a similar cell which was purged and evacuated but not treated with $D_2O$ gave a very large water vapor signal, and a similar cell which contained about 5 g of anhydrous calcium sulfate desiccant but which was not treated with $D_2O$ resulted in a signal corresponding to 0.009 Torr of water vapor.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above and of the corresponding application(s), are hereby incorporated by reference.

What is claimed is:

1. A method for reducing interference signals in an optical apparatus for measuring water vapor, comprising the steps of:
   a) exchanging hydrogen atoms in the water vapor in the apparatus with a source of labile deuterium, whereby adsorbed water vapor is converted to heavy water; and
   b) sealing the apparatus, whereby reintroduction of water is prevented.

2. The method of claim 1 wherein the steps are performed in a vacuum compatible apparatus.

3. The method of claim 1 wherein the steps are performed during manufacture of the optical apparatus.

4. The method of claim 1 wherein the optical apparatus comprises subassemblies and the steps are performed in the manufacture of at least one of the subassemblies.

5. The method of claim 1 wherein the steps are performed during use of the optical apparatus.

6. The method of claim 1 wherein the source of labile deuterium comprises a gas.

7. The method of claim 6 wherein the source of labile deuterium comprises heavy water vapor.

8. The method of claim 1 wherein the source of labile deuterium comprises a low vapor pressure, labile deuterium source.

9. The method of claim 1 wherein the source of labile deuterium comprises a liquid.

10. The method of claim 1 wherein the source of labile deuterium comprises a deuterated solid.

11. The method of claim 1 wherein the source of labile deuterium comprises deuterated acid gas.

12. The method of claim 11 wherein the source of labile deuterium comprises deuterated hydrogen chloride.

13. The method of claim 11 wherein the source of labile deuterium comprises deuterated hydrogen bromide.

14. The method of claim 1 wherein the source of labile deuterium comprises a deuterated basic gas.

15. The method of claim 14 wherein the source of labile deuterium comprises deuterated ammonia.

16. The method of claim 9 wherein the source of labile deuterium comprises heavy water liquid.

17. The method of claim 9 wherein the source of labile deuterium comprises heavy water liquid treated with at least one acid.

18. The method of claim 9 wherein the source of labile deuterium comprises heavy water liquid treated with at least one base.

19. The method of claim 1 wherein the source of labile deuterium comprises deuterium gas, and further comprising the step of adding a catalyst for enhancing isotope exchange with surface water.

20. The method of claim 1 wherein the source of labile deuterium comprises deuterated alcohol liquid.

21. The method of claim 1 wherein the source of labile deuterium comprises deuterated alcohol vapor.

22. The method of claim 1 wherein the source of labile deuterium comprises deuterated methanol.

23. The method of claim 1, wherein the step of exchanging comprises the steps of:

exposing a selected portion of the apparatus to the deuterium source whereby the exchanging occurs in water that contaminates that portion of the apparatus; and continuing the step of exposing for a sufficient time to substantially delete interference signals.

24. The method of claim 23, wherein the step of exposing further comprises the step of flowing the labile deuterium source to the selected portion of the apparatus.

25. The method of claim 23, wherein the step of exposing further comprises the step of evacuating the air from the selected portion of the apparatus, thereby increasing the diffusion constant.

26. The method of claim 23, wherein the step of exposing further comprises the step of heating the selected portion of the apparatus.

27. The method of claim 26, wherein the step of heating the selected portion of the apparatus comprises the step of causing turbulent mixing in the selected portion of the apparatus.

28. The method of claim 1, further comprising the step of removing excess heavy water vapor prior to the step of sealing the apparatus.

29. The method of claim 10, further comprising the step of inserting the deuterated solid into the apparatus.

30. The method of claim 29, wherein the solid comprises a deuterated desiccant.

31. The method of claim 30, wherein the deuterated desiccant acts as a long-term isotopic ballast for the apparatus.

32. The method of claim 10, wherein the solid comprises a deuterated salt.

33. The method of claim 32, wherein the solid comprises deuterated calcium sulfate.

34. The method of claim 10, wherein the solid comprises a molecular sieve pre-treated with $D_2O$ vapor.

35. The method of claim 10, wherein the apparatus has a source chamber and further comprising the step of inserting the solid into the source chamber.

36. The method of claim 35, wherein the apparatus is a water vapor sensor and the step of inserting further comprises inserting a deuterium source chosen to have sufficient mass such that a deuterium/hydrogen ratio value remains close to unity for a lifetime of the water vapor sensor.

37. A device for reducing interference signals in an optical apparatus for measuring water vapor, the optical apparatus having a source and a sample region, said device comprising means for exchanging hydrogen atoms in the water vapor in the apparatus with a source of labile deuterium, whereby adsorbed water vapor is converted into heavy water, and means for sealing the optical apparatus to prevent reintroduction of water.

38. The device of claim 37, wherein the means for exchanging comprises a gas manifold attached to the source.

39. The device of claim 38, further comprising means for evacuating the gas manifold.

40. The device of claim 37, further comprising means for exposing the apparatus to a source of heavy water vapor.

41. The device of claim 37, further comprising means for providing an isotopic ballast.

42. The device of claim 41, wherein the isotopic ballast comprises a molecular sieve pre-treated with $D_2O$ vapor.

43. The device of claim 41, wherein the isotope ballast comprises $CaSO_4.2D_2O$.

44. The method of claim 1, wherein the optical apparatus is a diode laser spectrometer.

45. The method of claim 1, wherein the optical apparatus is a Fourier transform spectrometer.

46. The method of claim 1, wherein the step of exchanging is performed in a gas manifold.

47. The method of claim 46, wherein the step of exchanging is performed in an ambient pressure gas handling apparatus.

48. The method of claim 46, wherein the step of exchanging is performed in an elevated pressure gas handling apparatus.

49. The device of claim 37, wherein the optical apparatus is a diode laser spectrometer.

50. The device of claim 37, wherein the optical apparatus is a Fourier transform spectrometer.

51. The device of claim 37, said device further comprising means for exposing the optical apparatus to dry gas.

52. The device of claim 37, said device further comprising means for removing heavy water prior to sealing.

* * * * *